(12) United States Patent
Liu et al.

(10) Patent No.: US 10,556,134 B2
(45) Date of Patent: Feb. 11, 2020

(54) STABLE PERSONAL CARE CREAM COMPOSITION

(71) Applicant: Conopco, Inc., Englewood Cliffs, NJ (US)

(72) Inventors: Hongbo Liu, Shanghai (CN); Zhaoting Liu, Shanghai (CN); Anjing Lou, Seymour, CT (US); Xiaoli Wang, Shanghai (CN); Nan Yang, Wuhan (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/532,156

(22) PCT Filed: Nov. 26, 2015

(86) PCT No.: PCT/EP2015/077784
§ 371 (c)(1),
(2) Date: Jun. 1, 2017

(87) PCT Pub. No.: WO2016/087306
PCT Pub. Date: Jun. 9, 2016

(65) Prior Publication Data
US 2017/0266470 A1    Sep. 21, 2017

(30) Foreign Application Priority Data

Dec. 2, 2014   (WO) ............... PCT/CN2014/092765
Jan. 16, 2015  (EP) ..................................... 15151500

(51) Int. Cl.
| | | |
|---|---|---|
| *A61Q 17/04* | (2006.01) | |
| *A61K 8/29* | (2006.01) | |
| *A61K 8/81* | (2006.01) | |
| *A61Q 19/08* | (2006.01) | |
| *A61K 8/06* | (2006.01) | |
| *A61K 8/27* | (2006.01) | |

(52) U.S. Cl.
CPC .............. *A61Q 17/04* (2013.01); *A61K 8/062* (2013.01); *A61K 8/27* (2013.01); *A61K 8/29* (2013.01); *A61K 8/8111* (2013.01); *A61Q 19/08* (2013.01); *A61K 2800/596* (2013.01)

(58) Field of Classification Search
CPC .... A61K 2800/596; A61K 8/062; A61K 8/27; A61K 8/29; A61K 8/8111; A61Q 17/04; A61Q 19/08
See application file for complete search history.

(56) References Cited

U.S. PATENT DOCUMENTS

| | | |
|---|---|---|
| 5,733,895 A | 3/1998 | Forestier et al. |
| 5,882,657 A | 3/1999 | Miguel-Colombel et al. |
| 2003/0113283 A1 | 6/2003 | Mattai et al. |
| 2003/0147830 A1 | 8/2003 | Phillips et al. |
| 2008/0242573 A1 | 10/2008 | Wei |
| 2015/0175724 A1 | 6/2015 | Klostermann et al. |
| 2017/0266470 A1 | 9/2017 | Liu et al. |

FOREIGN PATENT DOCUMENTS

| | | |
|---|---|---|
| CN | 104640536 | 5/2015 |
| EP | 0654989 | 9/1997 |
| EP | 0829259 | 3/1998 |
| EP | 2886102 | 6/2015 |
| EP | 2921157 | 9/2015 |
| JP | 11335240 | 12/1999 |
| WO | WO9404131 | 3/1994 |
| WO | WO9732560 | 9/1997 |
| WO | WO2014111571 | 7/2014 |
| WO | WO2015163980 | 11/2015 |

OTHER PUBLICATIONS

Aleksandra Zielinska et al., Fatty acids in vegetable oils and their importance in cosmetic industry, Science Technique CHEMIK, 2014, pp. 107-110; XP055241974; http://www.chemikinternational.com/wp-content/uploads/2014/02/2_14_4.pdf.
George Deckner, Carbomers: Overview, Resources & Materials, Prospector, 2013, pp. 1-3; XP055196379; http://knowledge.ulprospector.com/261/carbomers.
IPRP2 in PCTEP2015077784, Feb. 28, 2017.
Search Report and Written Opinion in EP15151500, dated Jun. 29, 2015.
Search Report and Written Opinion in PCTEP2015077784, dated Jan. 25, 2016.
Written Opinion in PCTEP2015077784, dated Oct. 28, 2016.
Momentive Inventing Possibilities Technical Data Sheet; Tospearl 145A; Mar. 13, 2018; pp. 1-5.
Ultrafine Zinc Oxide; Ultrafine Zinc Oxide Powder Sumitomo; Dec. 13, 2018; p. 1.
Parsol Unlimited DSM; Parsol SLX; Parsol DSM; 2000; pp. 1-2.
Lubrizol Personal Care Product Data Sheet; Carbopol 940 polymer; Feb. 23, 2017; pp. 1-2.
Tego Sun T 805 Technical Information; Hydrophobically Modified Microfine Titanium Dioxide; Apr. 2012; pp. 1-6.
Momentive Marketinig Buleetin, Tospearl Microspheres; 2003; pp. 1-8.
Notice of Opposition in EP15800872 (EP3226829) (P&G); Dec. 5, 2018.

*Primary Examiner* — Mark V Stevens
(74) *Attorney, Agent, or Firm* — Ellen Plotkin

(57) ABSTRACT

The invention relates to a personal care cream composition, more particularly to a photo-protective composition that maintains its sensory properties while ensuring high sun-protection efficacy. The present inventors have herein determined that inclusion of hydrophobic polymer particles of a specified particle size range enables certain cream compositions to not only provide the sunscreen benefits but also deliver the excellent watery sensation the consumers have come to expect from such compositions.

14 Claims, No Drawings

STABLE PERSONAL CARE CREAM COMPOSITION

FIELD OF THE INVENTION

The invention relates to a personal care cream composition. The invention more particularly relates to a photoprotective personal care composition that maintains its sensory properties while ensuring high sun-protection efficacy.

BACKGROUND OF THE INVENTION

Solar radiation includes about 5% ultraviolet (UV) radiation, wavelength of which is between 200 nm and 400 nm. It is further classified into three regions: from 320 to 400 nm (UV-A), 290 to 320 nm (UV-B) and from 200 to 290 nm (UV-C). A large part of UV-C radiation is absorbed by the ozone layer. Scientific studies have indicated that exposure to UV-A and UV-B radiation for short period causes reddening of the skin and localized irritation, whereas continued and prolonged exposure can lead to sunburn, melanoma and formation of wrinkles. It is also reported that UV radiation causes significant damage to hair. Therefore, it is desirable to protect the skin and other keratinous substrates of the human body from the harmful effects of both, UV-A and UV-B radiation.

Various cosmetic preparations have been reported for preventing and/or protecting the skin from harmful effects of ultraviolet radiation. Numerous organic sunscreen agents capable of absorbing UV-A rays are reported in the field of cosmetics. Many UV-B sunscreens are also known and approved for safe use in personal care compositions for protection from UV-B radiation.

Inorganic sunscreens, also known as inorganic sunblocks, are also used in photoprotective compositions. They work by blocking out the rays of the sun, no matter what the wavelength. They are included in such compositions in carefully calculated amounts and in carefully determined particles sizes. This is necessary since a choice of the wrong particle size or amount leads to either poor sensories on application of the composition on the skin or an unnatural whitish appearance when applied on the skin. Commonly used inorganic particles are zinc oxide, iron oxide, silica, mica, titanium dioxide or coloured pigment particles.

Cosmetic compositions are formulated in various cosmetically acceptable vehicles (or bases) depending on the sensory properties desired. Compositions may be formulated in an anhydrous vehicle or a water containing vehicle. Compositions comprising water may be formulated as a gel or as an emulsion. Gels are generally compositions comprising predominantly water with minimal or no oily phase. Composition comprising both water and oily phase are formulated as emulsions which may be an oil-in-water emulsion or a water-in-oil emulsion. The difference between these two types of emulsion is that although the ranges of water and oil overlap, the difference is in whether water is the dispersed phase or the continuous phase and vice-versa. The present invention relates to a water containing composition in the form of a oil-in-water emulsion which comprises fatty acid or an ester thereof and a cross-linked acrylic acid polymer. This type of a composition gives an emulsion in a lamellar phase. When such compositions are rubbed on to the skin they give a watery sensation which are liked by many consumers. When such compositions are to be formulated for sunscreen benefits, by including inorganic particles in them, they tend to cause an inordinate increase in the viscosity of the compositions. Concomitantly they affect the tactile sensory appeal of the compositions when they are rubbed on to skin. It is thus a problem to incorporate even small amounts of inorganic particles in such compositions without affecting the sensory appeal. The present inventors have, through extensive experimentation determined that inclusion of hydrophobic polymer particles of a specified particle size range enables such compositions to not only provide the sunscreen benefits but also deliver the excellent watery sensation the consumers have come to expect from such compositions.

US2008242573 (Procter & Gamble) relates to a multi-phase personal care composition which comprises an aqueous structured surfactant phase, a structuring system, and a benefit phase. The aqueous structured surfactant phase comprises from about 5 percent to about 16 percent, by weight of the multiphase personal care composition, of a lathering surfactant selected from the group consisting of anionic surfactants, nonionic surfactants, amphoteric surfactants, cationic surfactants or mixtures thereof and a structuring system. The structuring system comprises a non-ionic emulsifier having an HLB of from about 1.4 to about 13 by weight of the multiphase personal care composition, of an associative polymer; and an electrolyte. The benefit phase comprises from about 5 percent to about 30 percent, by weight of the multiphase personal care composition, of hydrophobic benefit material. The present invention differs from this published document in that this publication discloses that fatty acid is not included in such compositions. Therefore it can be inferred that such compositions do not deliver the sensory properties expected from such compositions.

It is thus an object of the present invention to provide for sunscreen compositions that exhibit the consumer preferred watery sensation from such compositions comprising a fatty acid or a ester thereof and a cross-linked acrylic acid polymer.

SUMMARY OF THE INVENTION

The present invention relates to a personal care cream composition comprising
(a) 0.1 to 2% by weight of the composition, inorganic particles having a mean particle size in the range of 2 to 500 nm;
(b) 0.1 to 2% by weight of the composition, hydrophobic polymeric particles having a mean particle size in the range of 1 to 10 microns; and
(c) a cosmetically acceptable base comprising (i) 1 to 8% fatty acid or an ester thereof, by weight of the composition (ii) 0.05 to 1% cross-linked acrylic acid polymer, by weight of the composition; and (iii) water.

It is particularly preferred that the composition has a viscosity in the range of 40,000 to 70,000 cps at 25° C.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "A personal care composition" as used herein, is meant to include a composition for topical application to the skin and/or hair of mammals, especially humans. Such a composition may be generally classified as leave-on or rinse off, and includes any product applied to a human body for additionally improving the appearance, cleansing, odor control or general aesthetics. It is more preferably a leave-on product. The composition of the present invention is in the form of cream. "Skin" as used herein is meant to include skin on the face and body (e.g. neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

By particle size, as per the present invention, is meant the average diameter when the particle is substantially spherical. When the particle is not substantially spherical, the particle size refers to the average leading dimension of the particles. In the case of the present invention, the average particle size of the inorganic particles is generally measured using light scattering techniques. In the case of the present invention, the average particle size of the hydrophobic polymeric particles are measured using sieve analysis.

By way of the present invention it is possible to prepare personal care compositions in the viscosity range of 40,000 to 70,000 cps at 25° C.

The present invention relates to a personal care cream composition comprising inorganic particles; hydrophobic polymeric particles; and a cosmetically acceptable base comprising fatty acid or an ester thereof, cross-linked acrylic acid polymer; and water. The composition preferably has a viscosity in the range of 40,000 to 70,000 cps at 25° C. The viscosity of the composition in the above range is measured using a Brookfield viscometer RVT, Model D220, using a T-bar spindle D at 5 RPM, 60 seconds at 25° C.

It is preferred that inorganic particles are selected from titanium dioxide, zinc oxide, mica, iron oxide, a pigment or combinations thereof. More preferably the the inorganic particle is titanium dioxide or zinc oxide. The inorganic particle has a mean particle size in the range of 2 to 500 nm, preferably in the range of 10 to 400 nm, more preferably in the range of 20 to 300 nm. By the particle size herein is meant the primary particle size and not the particle size of the agglomerated mass of particles. The inorganic particle is present in 0.1 to 2%, preferably 0.3 to 1.8%, more preferably 0.5 to 1.5% by weight of the composition. The inorganic particles are preferably coated. Preferred coating materials are stearic acid or alumina. An especially preferred particle for use in the present invention is titanium dioxide under the brand name of MT 700Z available from Tayca.

The composition of the invention comprises hydrophobic polymeric particles. Hydrophobic polymeric particles as per this invention are preferably organic polymers. Hydrophobic polymeric particles as per the present invention are such that when included in an emulsion, these particles substantially partition into the oil phase. The oil phase in an emulsion can be an internal phase for oil in water emulsion, or an external phase for water in oil emulsion. Hydrophobic polymeric particles are preferably selected from polyethylene, polypropylene or silicone resin beads more preferably polyethylene. An especially suitable hydrophobic polymeric particle is sold under the name of LE-1080 from Sumitomo Corpcan be sourced from The hydrophobic polymeric particle is present in 0.1 to 2%, preferably 0.3 to 1.8%, more preferably 0.5 to 1.5% by weight of the composition.

Without wishing to be bound by theory it is believed that the inclusion of the hydrophobic polymeric particles results in the increase of the internal phase volume by enlarging the internal droplet size, which in turn enhances the desired water slip phenomenon during the application under certain shear.

The composition of the invention comprises a cosmetically acceptable base which comprises a fatty acid or an ester thereof. It is more preferably a fatty acid. Most preferred fatty acid is stearic acid. The fatty acid or an ester thereof preferably has 12 to 22 carbon atoms, more preferably 14 to 18 carbon atoms. The composition preferably comprises 1 to 8%, preferably 2 to 5 wt % fatty acid or ester thereof.

The composition as per the invention comprises a cross-linked acrylic acid polymers. They are generally a a homopolymer of acrylic acid with a high molecular weight, which is cross-linked with any of several polyalcohol allyl ethers. They are usually referred to as carbomers. A highly suitable cross linked acrylic acid polymer is available as Acrylpol 980 from AAKO. Cross-linked acrylic acid polymers are preferably included in 0.05 to 1.0%, preferably from 0.1 to 1%, further more preferably from 0.1 to 0.6% by weight of the composition.

An important aspect of the present invention is that the cosmetically acceptable base provides the desired baseline sensorials. It is especially important that the fatty acid or ester thereof is present in 1 to 8% by weight of the composition and the cross-linked acrylic acid polymer is present in 0.05 to 1% by weight of the composition. This unique combination provides the desired watery sensation the consumers expect from such compositions. At lower concentrations of these base materials the consumers experience a sticky sensation and at higher concentrations they experience a heavy sensation that is often observed in highly viscous compositions, both of which are undesirable. In order to get even better sensorials, it is preferred that the weight ratio of the fatty acid or ester thereof to the cross-linked acrylic acid polymer is in the range of 4:1 to 16:1, further more preferably 8:1 to 12:1.

The composition of the invention preferably additionally comprises an oily material. Preferred oily materials are mineral oil, isopropyl myristate, silicone oil or mixtures thereof. The oily material preferably is present in 1-10% by weight of the composition. When mineral oil is present, it is preferred to be included in 1 to 5% by weight of the composition. When silicone oil is present, it is preferred to be included in 0.1 to 2% by weight of the composition. When isopropyl myristate is present, it is preferably included in 1 to 6% by weight of the composition. Without wishing to be bound by theory it is believed that the oily materials are included in the formulation to generate an emulsion structure that improves the application smoothness. When a specific oil has been selected the amount that needs to be included will dictate the optimization of the internal and external phase ratio.

It is preferred that the composition is prepared as an emulsion by way of use of an emulsifier. Suitable emulsifiers are a non-ionic surfactant, anionic surfactant or cationicsurfactant, preferably a non-ionic surfactant. The non-ionic surfactant is preferably selected from the class of fatty alcohol ethoxylates, alkyl phenol ethoxylates or polyoxyethylene sorbitan alkyl esters. Non-ionic surfactant of the fatty alcohol ethoxylates which may be used in the present invention are sold under the generic brand name of Brij. Non-ionic surfactant of the alkyl phenol ethoxylates which may be used in the present invention are sold under the generic brand name of Triton. Non-ionic surfactant of the polyoxyethylene sorbitan alkyl esters which may be used in the present invention are sold under the generic brand name of Tween.

The non-ionic surfactant is present in 0.1 to 5%, preferably 1 to 4% by weight of the composition.

Total amount of emulsifier is preferably included in 0.2 to 5% preferably from 0.5 to 3% by weight of the composition.

The composition for the invention may additionally comprise fatty alcohol which may be preferably included in 0.1 to 2% by weight of the composition. Preferred fatty alcohol is cetyl alcohol. The composition comprises water. Water is preferably included in 30 to 90%, preferably 40 to 85% by weight of the composition.

The composition preferably exhibits a pH in the range of 5.5 to 7.5 as measured at 25° C.

The composition may optionally comprises an organic sunscreen. When present, organic sunscreen may be included in 0.1 to 15%, preferably 0.5 to 8% by weight of the composition. Organic sunscreens are preferably chosen from the following seven major groups: (1) benzophenones, (2) anthranilates, (3) dibenzoylmethanes (4) salicylates, (5) cinnamates, (6) camphores and (7) p-amino benzoic acid (PABA) or their derivatives or mixtures. The organic sunscreens may be of the UV-A or of the UV-B sunscreen types. Preferred UV-A sunscreen is a dibenzoylmethane, triazine, triazone, or benzophenone derivative. A more preferred UV-A sunscreen belongs to the dibenzoylmethane group. When present, this is included in 0.1 to 5% dibenzoylmethane or its derivative. The most preferred dibenzoylmethane derivative is 4-tert.-butyl-4'-methoxydibenzoylmethane. Dibenzoylmethane or its derivative is preferably present in 0.2 to 5%, more preferably 0.4 to 3% by weight of the composition.

The composition of the invention may comprise a UV-B sunscreen. UV-B organic sunscreen is preferably selected from the class of cinnamic acid, salicylic acid, diphenyl acrylic acid or derivatives thereof. A few of the preferred oil soluble UV-B sunscreens which are commercially available and useful for inclusion in the composition of the invention are Octisalate™, Homosalate™, NeoHelipan™, Octocrylene™, Oxybenzone™ or Parsol MCX™. When present, UVB sunscreen is included in 0.1 to 7%, preferably from 0.5 to 6%, more preferably 1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Another aspect of the present invention relates to a method of providing photoprotection to the skin comprising the step of applying a composition of the invention on to the desired surface of skin.

The invention is now further described by way of the following non-limiting examples.

EXAMPLES

The following cream formulations were prepared.

| Ingredients | Example A Wt % | Example B Wt % | Example 1 Wt % |
|---|---|---|---|
| Glycerin | 1.00 | 1.00 | 1.00 |
| Sodium Hydroxide (solution) | 0.05 | 0.05 | 0.05 |
| Carbomer (Acrypol 980) | 0.4 | 0.4 | 0.2 |
| Stearic acid | 3 | 3 | 3 |
| Cetyl Alcohol | 0.5 | 0.5 | 0.5 |
| Isopropyl Myrsitate | 4 | 4 | 4 |
| Mineral oil | 1.5 | 1.5 | 1.5 |
| Glyceryl monostearate | 1.5 | 1.5 | 1.5 |
| Dimethicone fluid, 200 cst | 0.5 | 0.5 | 0.5 |
| Parsol MCX | 1.25 | 1.25 | 1.25 |
| Parsol 1789 | 0.4 | 0.4 | 0.4 |
| Triethanolamine | 1 | 1 | 1 |
| Niacinamide | 3 | 3 | 3 |
| TiO2 MT700Z[1] | 0 | 1.0 | 1.0 |
| PE beads [2] | 0 | 0.0 | 0.5 |
| Water | To 100 | To 100 | To 100 |

[1] TiO2 MT700Z is a sample of titanium dioxide with an average particle size of 80 nm procured from Tayca Corporation.
[2] PE beads is a sample of polyethylene beads of average particle size of 6 microns procured from Sumitomo Corporation.

The above three cream samples were subjected to analysis using the following procedure:

MSV is the Maximum Stress Variation, the maximum difference of the measured stress to the Herschel-Bulkley model fitting curve.

Higher the MSV, the farther away the measured curve is from the Herschel-Bulkey model fitting curve. This generally implies that there is a stronger wall slip and therefore a more watery sensorial when the cream is rubbed on to the skin. It is also known that wall slip and watering feel will disappear with increase of friction coefficient. The MSV and Friction coefficient were measured using the following procedure:

Viscosity Test

After storage at room temperature (about 25° C.) for 1 day, the viscosity of each sample was measured by a rheometer (Anton Paar Rheometer MCR501, Austria) system using parallel plate geometry (PP50/TG) at 25° C. The gap used was 0.5 mm and the shear rate range was from 0.1 $s^{-1}$ to 1000 $s^{-1}$. The resultant shear stress at high shear rate (from around above 10 $s^{-1}$ to 1000 $s^{-1}$) was then fitted to the Herschel-Bulkley Model: $\tau=\tau_y+K_\gamma\&^P$ using the data analysis software of Anton Paar (RheoPlus). The fitting curve was extended to low shear rates. The maximum stress variation (MSV) is defined as the biggest difference between the measured stress and the fitting result from Herschel-Bulkley Model at low shear rates.

Film Friction Coefficient Test

The friction coefficient of the film formed by the composition of the present invention was measured at 23° C. and relative humidity of 45% by a home-made instrument, a motor driven mechanical finger, with accelerometers and loading cells.

0.125 g sample was spread evenly on a bio-skin strip (Color: 30#, ex. BEAU LAX, Co. Ltd., Tokyo, Japan) with size of 2.5 cm×13 cm. After naturally drying for two hours, the bio-skin strip was placed onto the sample station. The mechanical finger with attached piece of glove rubber was used to rub the bio-skin strip with fixed force which is perpendicular to the strip. Loading cells under the strip recorded the normal force experienced by the substrate under the rub of the finger. Then the friction coefficient for the interface between the finger and strip with sample was calculated according to paper by Akay et al. (Wear, Volume 276-277, 2012, Pages 61-69). The friction coefficient for naked bio-skin strip was also measured by the same method without spreading sample. If the friction coefficient of sample film/finger is greater than the naked bio-skin strip/finger, the sample would deliver "draggy" benefits to consumer.

The data on the MSV, viscosity and friction coefficient are summarized for the three samples below:

|  | Example | Example B | Example 1 |
| --- | --- | --- | --- |
| MSV (Pa) | 34.4 | 0.0 | 31.8 |
| Friction Coefficient | 0.38 | 0.60 | 0.41 |
| MSV | 57.9 | 108 | 43.7 |
| Viscosity (cps)* | 49200 | 63600 | 44400 |

*The viscosity is measured using a Brookfield viscometer RVT, Model D220, using a T-bar spindle D at 5 RPM, 60 seconds at 25° C.

The data in the table above indicates that the value of MSV reduces and the value of friction coefficient increases on inclusion of 1% inorganic particle (TiO$_2$) (Example B) in a base formulation (Example A). These values of Example B are indicative of a less watery feel on rubbing the composition on skin. When additionally 0.5% polyethylene beads are included in the composition (Example 1) the watery feel is recovered as evidenced by the lowered value of friction coefficient and the increase in the value of MSV, with values similar to that of the base formulation (Example A). The inclusion of TiO$_2$ particles additionally provides the desired sunscreen benefits.

The invention claimed is:

1. A personal care cream composition comprising
   (a) 0.1 to 2% by weight of the composition, inorganic particles having a mean particle size in the range of 20 to 300 nm;
   (b) 0.1 to 2% by weight of the composition, hydrophobic polymeric particles comprising polyethylene having a mean particle size in the range of 1 to 10 microns; and
   (c) a cosmetically acceptable base comprising (i) 1 to 8% of fatty acid or an ester thereof, by weight of the composition; (ii) 0.05 to 1% of a cross-linked acrylic acid polymer, by weight of the composition; and (iii) water;
   wherein the weight ratio of the fatty acid or ester thereof to the cross-linked acrylic acid polymer is in the range of 4:1 to 16:1; and
   wherein the composition has a viscosity from 40,000 to 70,000 cps at 25° C. and the composition further comprises nonionic emulsifier.

2. The composition as claimed in claim 1 wherein the inorganic particle is selected from titanium dioxide, zinc oxide, mica, iron oxide, a pigment or combinations thereof and the nonionic emulsifier is a fatty alcohol ethoxylate.

3. The composition as claimed in claim 2 wherein the inorganic particle is titanium dioxide or zinc oxide.

4. The composition as claimed in claim 1 wherein said fatty acid or an ester thereof has 12 to 22 carbon atoms.

5. The composition as claimed in claim 1 comprising 2 to 5% by weight of the composition, fatty acid or ester thereof.

6. The composition as claimed in claim 1 comprising 0.1 to 1% by weight of the composition, cross-linked acrylic acid polymer.

7. The composition as claimed in claim 1 wherein hydrophobic polymer particle makes up from 0.3 to 1.8% by weight of the composition, the fatty acid or ester thereof has 14 to 18 carbon atoms, and further wherein the composition comprises mineral oil and the mineral oil is present at 1 to 5% by weight and/or the composition comprises silicone oil and the silicone oil is present at 0.1 to 2% by weight.

8. The composition as claimed in claim 1 additionally comprising an oily material selected from mineral oil, silicone oil or mixtures thereof.

9. The composition as claimed in claim 8 comprising 1-10% by weight of the composition of the oily material.

10. The composition as claimed in claim 1 additionally comprising fatty alcohol.

11. The composition as claimed in claim 10 comprising 0.1 to 2% by weight of the composition of a fatty alcohol.

12. The composition as claimed in claim 1 comprising 30 to 90% water by weight of the composition.

13. A method of providing photoprotection to skin comprising the step of applying the composition as claimed in claim 1 on to a desired surface of the skin.

14. The composition as claimed in claim 1 wherein the fatty ester comprises isopropyl myristate.

* * * * *